(12) United States Patent
Shmarev et al.

(10) Patent No.: US 8,189,203 B2
(45) Date of Patent: May 29, 2012

(54) RETICLE INSPECTION SYSTEMS AND METHOD

(75) Inventors: Yevgeniy Konstantinovich Shmarev, Lagrangeville, NY (US); Eric Brian Catey, Danbury, CT (US); Robert Albert Tharaldsen, Sherman, CT (US); Richard David Jacobs, Brookfield, CT (US)

(73) Assignee: ASML Holding N.V., Veldhoven (NL)

( * ) Notice: Subject to any disclaimer, the term of this patent is extended or adjusted under 35 U.S.C. 154(b) by 480 days.

(21) Appl. No.: 12/573,408

(22) Filed: Oct. 5, 2009

(65) Prior Publication Data

US 2010/0149548 A1 Jun. 17, 2010

Related U.S. Application Data

(60) Provisional application No. 61/122,488, filed on Dec. 15, 2008.

(51) Int. Cl.
*G01B 11/02* (2006.01)
(52) U.S. Cl. .................. 356/511; 356/237.4; 356/237.5; 382/141; 382/144
(58) Field of Classification Search .... 356/237.1–241.6, 356/450–521; 430/5, 311, 313, 394; 382/141, 382/143, 145, 152
See application file for complete search history.

(56) References Cited

U.S. PATENT DOCUMENTS

| | | | | |
|---|---|---|---|---|
| 5,426,203 A | * | 6/1995 | Sohn et al. | .......... 556/137 |
| 5,548,401 A | * | 8/1996 | Ozaki | .......... 356/239.3 |
| 2002/0025479 A1 | * | 2/2002 | Okamoto et al. | .......... 430/5 |
| 2005/0179907 A1 | * | 8/2005 | Feldman | .......... 356/489 |
| 2007/0258086 A1 | | 11/2007 | Bleeker et al. | |

FOREIGN PATENT DOCUMENTS

| | | |
|---|---|---|
| JP | 2-024539 A | 1/1990 |
| JP | 4-127150 A | 4/1992 |
| JP | 6-019119 A | 1/1994 |
| JP | 6-082381 A | 3/1994 |
| JP | 2002-049143 A | 2/2002 |
| JP | 2007-333729 A | 12/2007 |

OTHER PUBLICATIONS

English-Language Translation of Notice of Reasons for Rejection directed to related Japanese Patent Application No. 2009-278112, mailed Jun. 20, 2011, Japanese Patent Office; 6 pages.

* cited by examiner

*Primary Examiner* — Tarifur Chowdhury
*Assistant Examiner* — Michael P Lapage
(74) *Attorney, Agent, or Firm* — Sterne, Kessler, Goldstein & Fox P.L.L.C.

(57) ABSTRACT

A method and systems for reticle inspection. The method includes coherently illuminating surfaces of an inspection reticle and a reference reticle, applying a Fourier transform to scattered light from the illuminated surfaces, shifting the phase of the transformed light from the reference reticle such that a phase difference between the transformed light from the inspection reticle and the transformed light from the reference reticle is 180 degrees, combining the transformed light as an image subtraction, applying an inverse Fourier transform to the combined light, and detecting the combined light at a detector. An optical path length difference between two optical paths from the illumination source to the detector is less than a coherence length of the illumination source. The image detected by the detector represents a difference in amplitude and phase distributions of the reticles allowing foreign particles, defects, or the like, to be easily distinguished.

20 Claims, 18 Drawing Sheets

RETICLE INSPECTION SYSTEMS AND METHOD

CROSS REFERENCE TO RELATED APPLICATION(S)

This application claims benefit under 35 U.S.C. §119(e) to U.S. Provisional Patent Application No. 61/122,488, filed Dec. 15, 2008, which is incorporated by reference in its entirety.

BACKGROUND

1. Field of the Invention

The present invention generally relates to lithography, and more particularly to inspection of reticles used for lithography.

2. Background Art

Lithography is widely recognized as a key process in manufacturing integrated circuits (ICs) as well as other devices and/or structures. A lithographic apparatus is a machine, used during lithography, which applies a desired pattern onto a substrate, such as onto a target portion of the substrate. During manufacture of ICs with a lithographic apparatus, a patterning device (which is alternatively referred to as a mask or a reticle) generates a circuit pattern to be formed on an individual layer in an IC. This pattern may be transferred onto the target portion (e.g., comprising part of, one, or several dies) on the substrate (e.g., a silicon wafer). Transfer of the pattern is typically via imaging onto a layer of radiation-sensitive material (e.g., resist) provided on the substrate. In general, a single substrate contains a network of adjacent target portions that are successively patterned. Manufacturing different layers of the IC often requires imaging different patterns on different layers with different reticles. Therefore, reticles must be changed during the lithographic process.

Current lithography systems project mask pattern features that are extremely small. Dust or extraneous particulate matter appearing on the surface of the reticle can adversely affect the resulting product. Any particulate matter that deposits on the reticle before or during a lithographic process is likely to distort features in the pattern being projected onto a substrate. Therefore, the smaller the feature size, the smaller the size of particles critical to eliminate from the reticle.

A pellicle is often used with a reticle. A pellicle is a thin transparent layer that may be stretched over a frame above the surface of a reticle. Pellicles are used to block particles from reaching the patterned side of a reticle surface. Although particles on the pellicle surface are out of the focal plane and should not form an image on the wafer being exposed, it is still preferable to keep the pellicle surfaces as particle-free as possible. For certain types of lithography (e.g., extreme ultraviolet (EUV) lithography), however, pellicles are not used. Because the EUV reticles are not covered, they are prone to particle contamination, which may cause defects in a lithographic process. Particles on EUV reticles are one of the main sources of imaging defects. Inspection and cleaning of an EUV reticle before moving the reticle to an exposure position can be an important aspect of a reticle handling process. Reticles are typically cleaned when contamination is suspected, as a result of inspection, or on the basis of historical statistics.

Reticles are typically inspected for defects using laser scanning scatterometer or imaging systems that use scattered light techniques. With this technique, a laser beam is focused on a reticle and a radiation beam that is scattered away from a specular reflection direction is detected. Particles on an object surface will randomly scatter the light. By observing the illuminated surface with a microscope, the particles will light up as bright spots. The intensity of the spots is a measure of the size of the particle.

A scatterometer operating with visible or ultraviolet (UV) light allows significantly faster reticle inspection than scanning imaging systems (e.g., confocal, EUV or electron beam microscope systems). There are known scatterometers that use a laser illumination beam and a coherent optical system with a Fourier filter in the pupil plane that blocks light diffracted from a pattern on the reticle. This type of scatterometer detects light scattered by particles over the level of background coming from a periodic pattern on the reticle.

One example of such a system is described in U.S. Pat. Application Publication No. 2007/0258086 A1 to Bleeker et al., published on Nov. 8, 2007, and entitled, "Inspection Method and Apparatus Using Same." As shown in FIG. 1, an exemplary inspection system 100 includes a channel 102 including a microscope objective 104, a pupil filter 106, a projection optical system 108, and detector 110. A radiation (e.g., laser) beam 112 illuminates an object (e.g., a reticle) 114. Pupil filter 106 is used to block optical scattering due to the pattern of object 114. A computer 116 can be used to control the filtering of pupil filter 106 based on the pattern of object 114. Accordingly, filter 106 is provided as a spatial filter in a pupil plane relative to object 114 and is associated with the patterned structure of object 114 so as to filter out radiation from the scattered radiation. Detector 110 detects a fraction of radiation that is transmitted by filter 106 for detection of contamination particles.

It is not feasible, however, to use an inspection system such as inspection system 100 on reticles having arbitrary (i.e., non-periodic) patterns. This limitation is a result of saturation of the detector by light diffracted by the pattern. The detector has limited dynamic range and cannot detect light from a particle in the presence of light scattered from the pattern. In other words, correspondent light can be efficiently filtered out by a spatial filter in a Fourier plane of a coherent optical system only for a periodic pattern. Even with a periodic pattern (e.g., for DRAM), there are significant issues when modifying a Fourier filter in a reticle scanning process. With an inspection system such as inspection system 100, there is also a limitation to use only a collimated illumination beam for its Fourier filtration. Therefore, it does not allow the illumination optimization necessary for suppression of scattering from reticle surface roughness.

Precision, quality, and certainty of particle detection is very often compromised when using known inspection systems. With increasing demands for higher throughput and shrinking lithographic feature sizes, it is becoming increasingly important to enhance an inspection system's performance in terms of speed, smaller particle size detection, and immunity against unwanted effects.

SUMMARY

Given the foregoing, what are needed are systems and methods for inspecting reticles having arbitrary patterns. To meet this need, embodiments of the present invention are directed to inspection systems and methods that allow particle and defect detection on reticles having arbitrary patterns.

For example, an embodiment of the present invention provides a method of inspecting a reticle. The method includes illuminating with a coherent illumination source respective portions of a surface of an inspection reticle and a surface of a reference reticle, applying a Fourier transform to scattered light from the illuminated portions, shifting the phase of the transformed light from the reference reticle such that a phase difference between the transformed light from the inspection reticle and the transformed light from the reference reticle is 180 degrees, combining the transformed light from the illuminated portions, applying an inverse Fourier transform to the combined light, and detecting the combined light at a detector. In this embodiment, an optical path length difference between a first optical path from the illumination source to the detector and a second optical path from the illumination source to the detector is less than a coherence length of the illumination source, and the combined light detected by the detector is in the form of an image representing a difference in amplitude and phase distributions of the inspection reticle and the reference reticle, allowing foreign particles and/or defects to be easily distinguished.

Another embodiment of the present invention provides a reticle inspection system that includes a coherent illumination source configured to illuminate respective portions of an inspection reticle and a reference reticle, an inspection interferometer branch having a first microscope objective system configured to apply a first Fourier transform to a first light beam propagated from the illuminated portion of the inspection reticle, and a reference interferometer branch having a second microscope objective system configured to apply a second Fourier transform to a second light beam propagated from the illuminated portion of the reference reticle. The system also includes an interferometer element configured to induce a 180-degree phase shift between the inspection interferometer branch and the reference interferometer branch. The system further includes a beam splitter configured to receive and combine the first and second light beams, a Fourier lens configured to provide an inverse Fourier transform to the combined first and second light beams, and a detector configured to detect the combined first and second light beams such that they form an image representing a difference in amplitude and phase distributions of the inspection reticle and the reference reticle. Foreign particles and/or defects are easily distinguishable in the image. In this embodiment, the inspection interferometer branch has an optical path between the inspection reticle and the detector and the reference interferometer branch has an optical path between the reference reticle and the detector. The optical path length difference between the inspection interferometer branch and the reference interferometer branch is less than a coherence length of the illumination source. In one embodiment, the system includes an interferometer element in the inspection interferometer branch that is configured to direct the first light beam from the first microscope objective system to the beam splitter. This interferometer element can be the same interferometer element used to induce the 180-degree phase shift. In an alternative embodiment, the system includes a first interferometer element configured to direct the first light beam from the first microscope objective system to the beam splitter, and a second interferometer element configured to direct the second light beam from the second microscope objective system to the beam splitter. Either of these interferometer elements can be used to induce the 180-degree phase shift.

A further embodiment of the invention provides a lithography system having a reticle inspection system as any of those described above.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention.

FIGS. 3A-D and 4 depict examples of reticle illumination, according to embodiments of the present invention.

Figure 5:
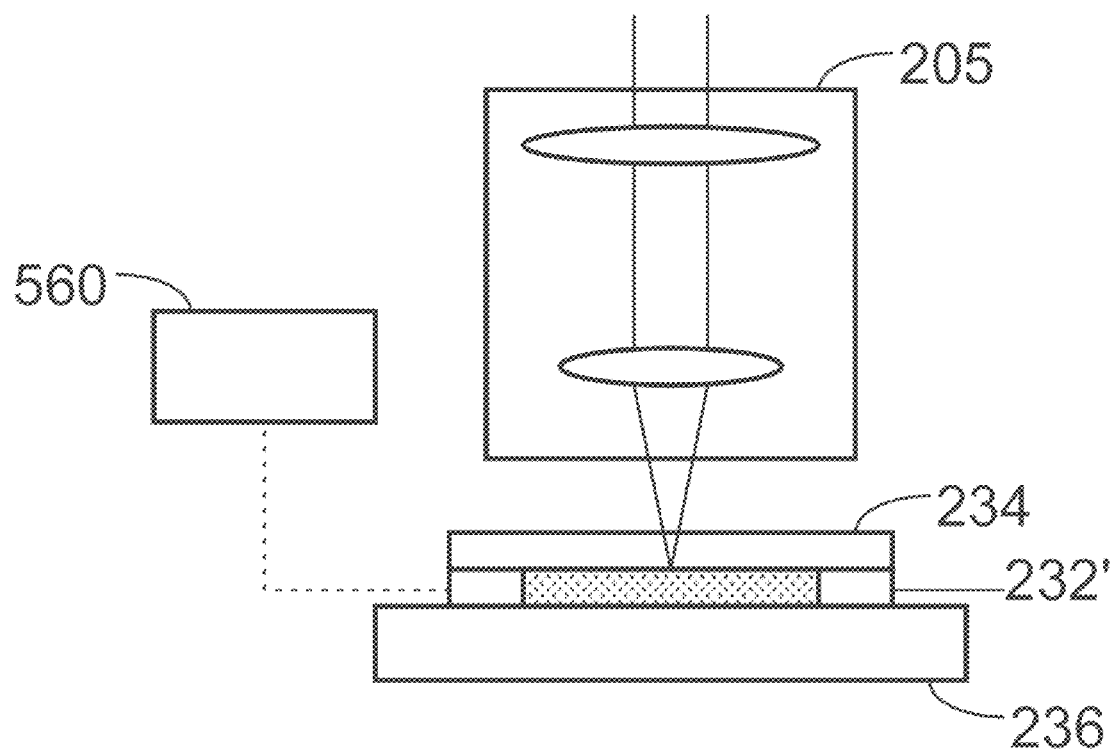

FIG. 5 depicts a spatial light modulator used as a reference reticle, according to an embodiment of the present invention.

Figure 6:
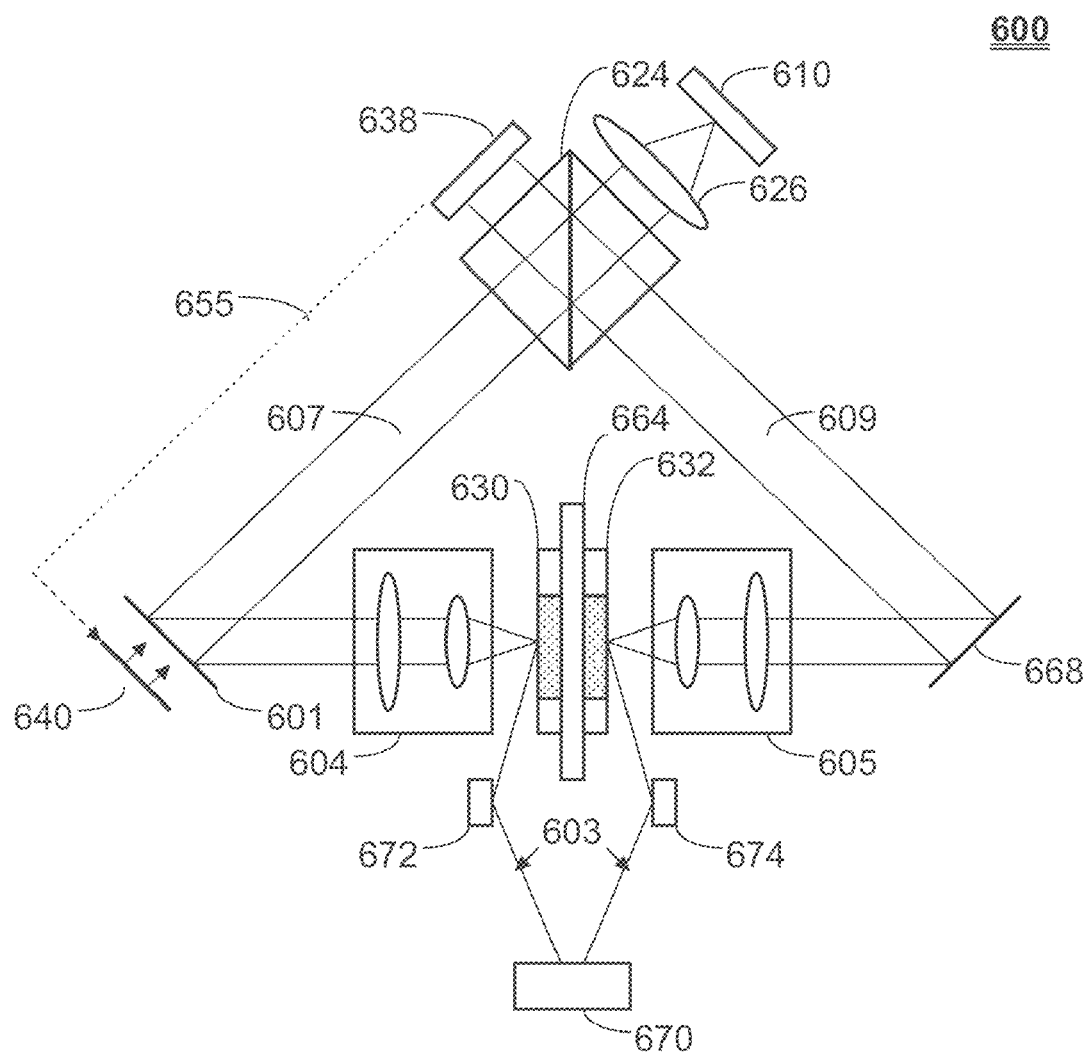

FIG. 6 depicts a reticle inspection system having equal optical path lengths, according to an embodiment of the present invention.

Figure 7A:
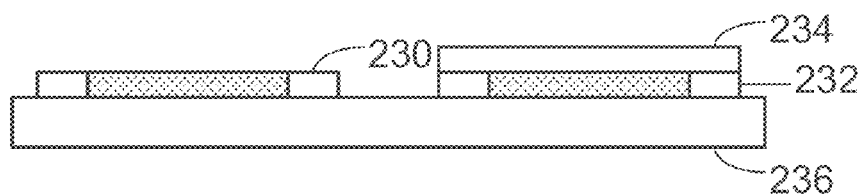
Figure 7B:
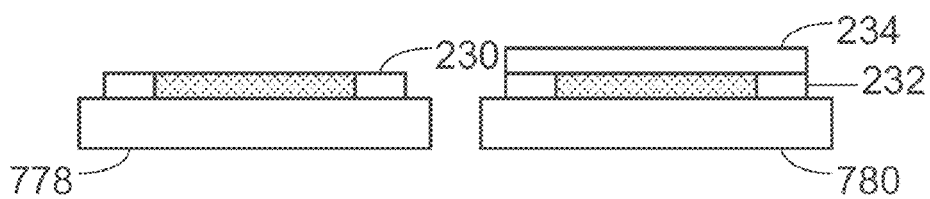
Figure 7C:
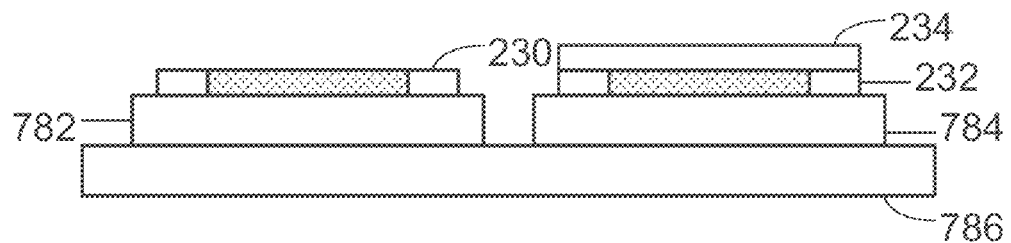

FIGS. 7A, 7B, and 7C depict alternative examples of reticle supports, according to embodiments of the present invention.

Figure 8A:
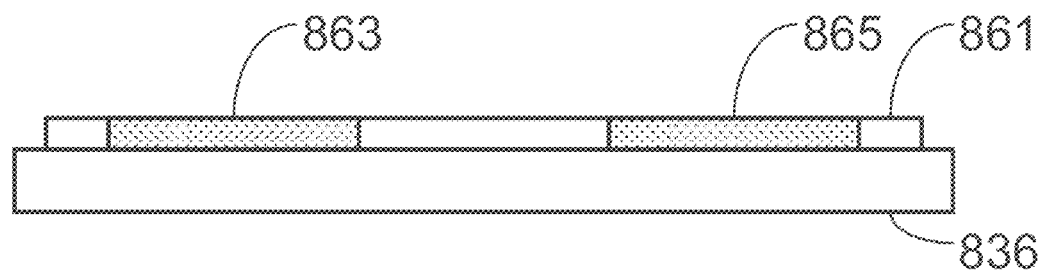
Figure 8B:
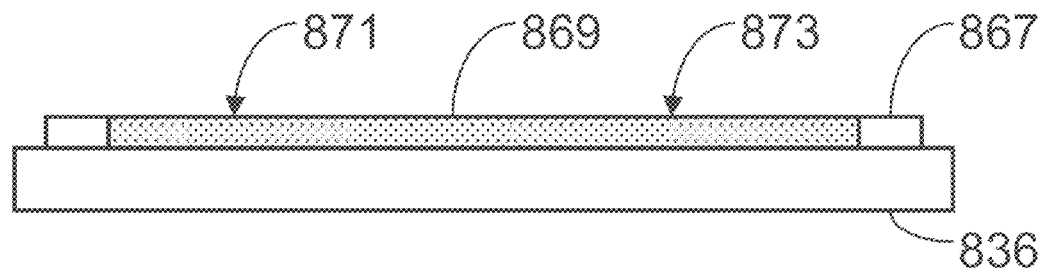

FIGS. 8A and 8B depict alternative examples using a single reticle, according to embodiments of the present invention.

Figure 9:
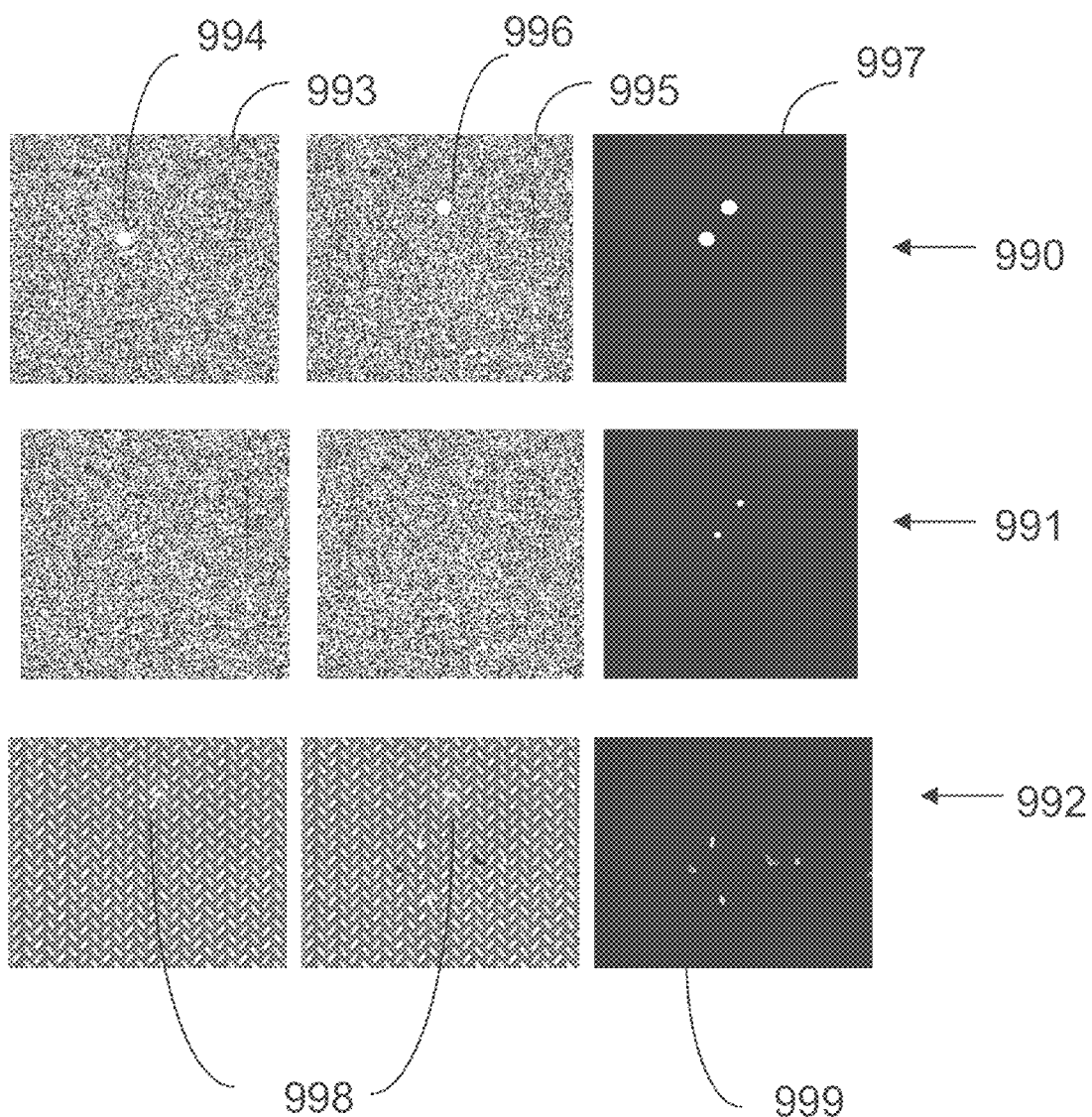

FIG. 9 illustrates imaging examples showing foreign particles detected using embodiments of the present invention.

Figure 10A:
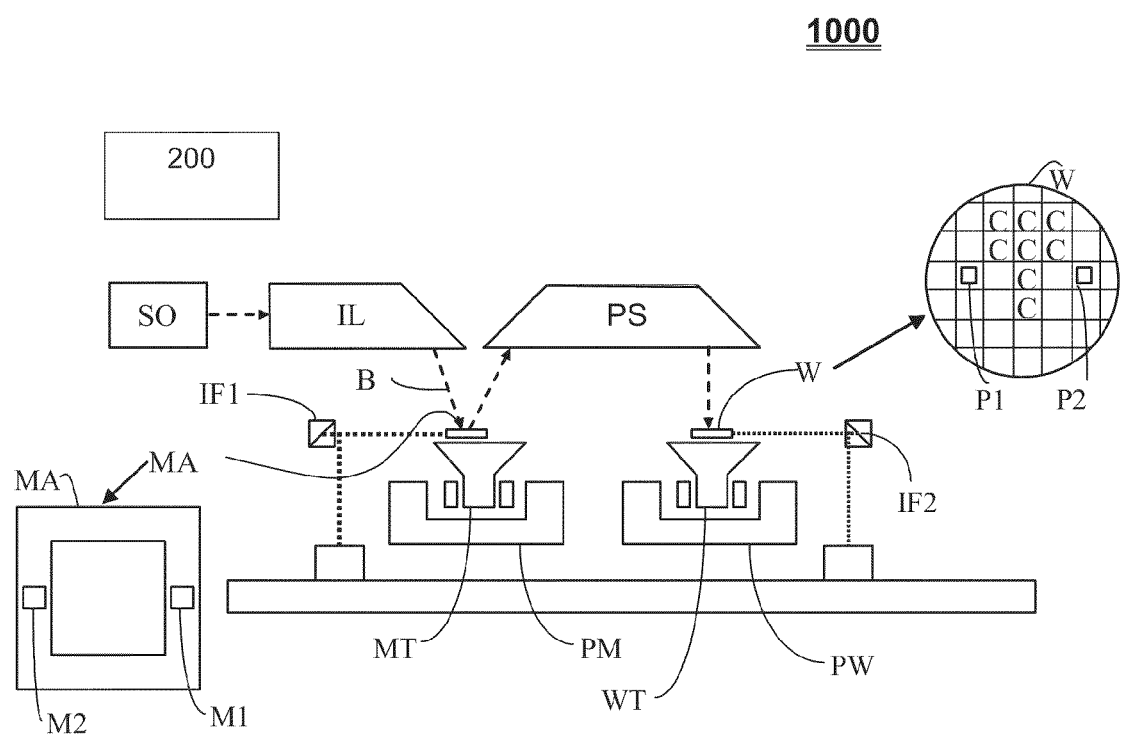
Figure 10B:
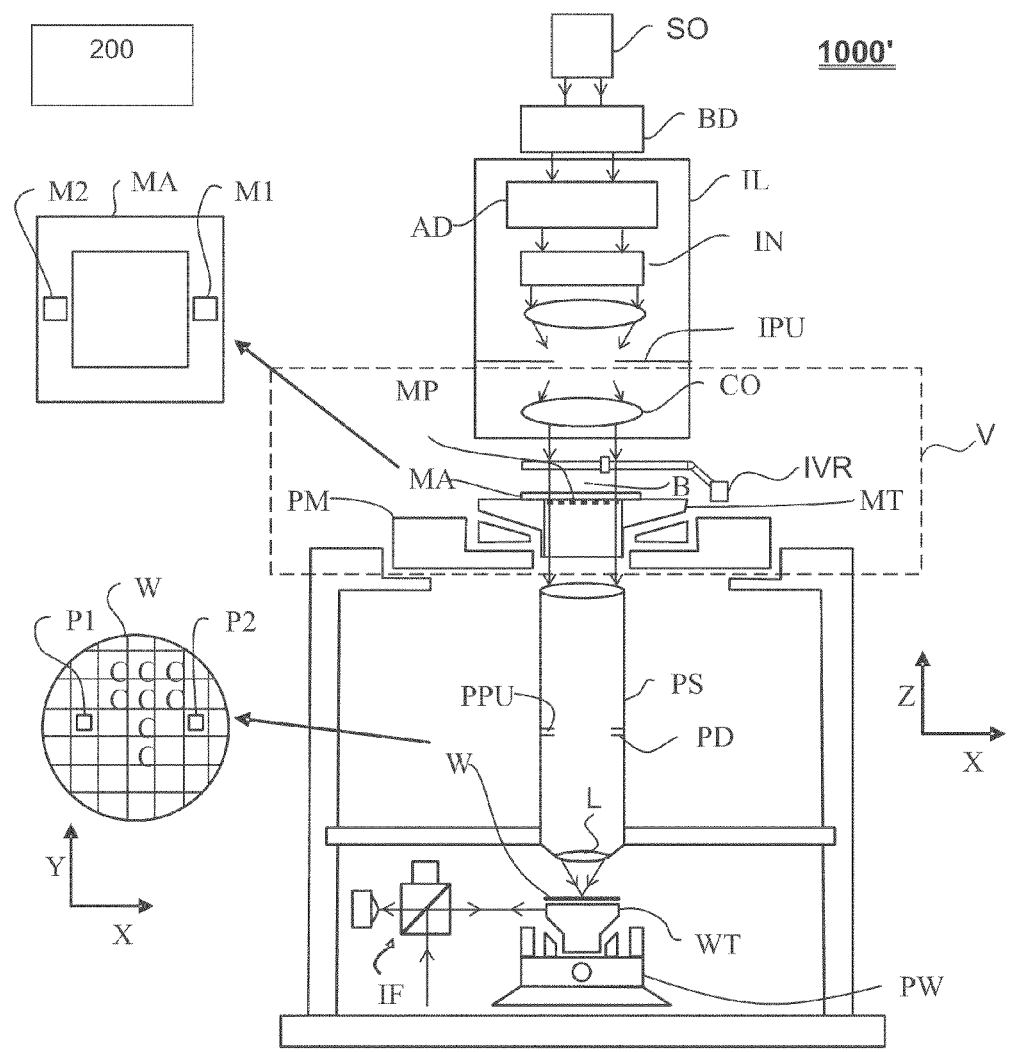

FIGS. 10A and 10B respectively depict reflective and transmissive lithographic apparatuses.

Figure 11:
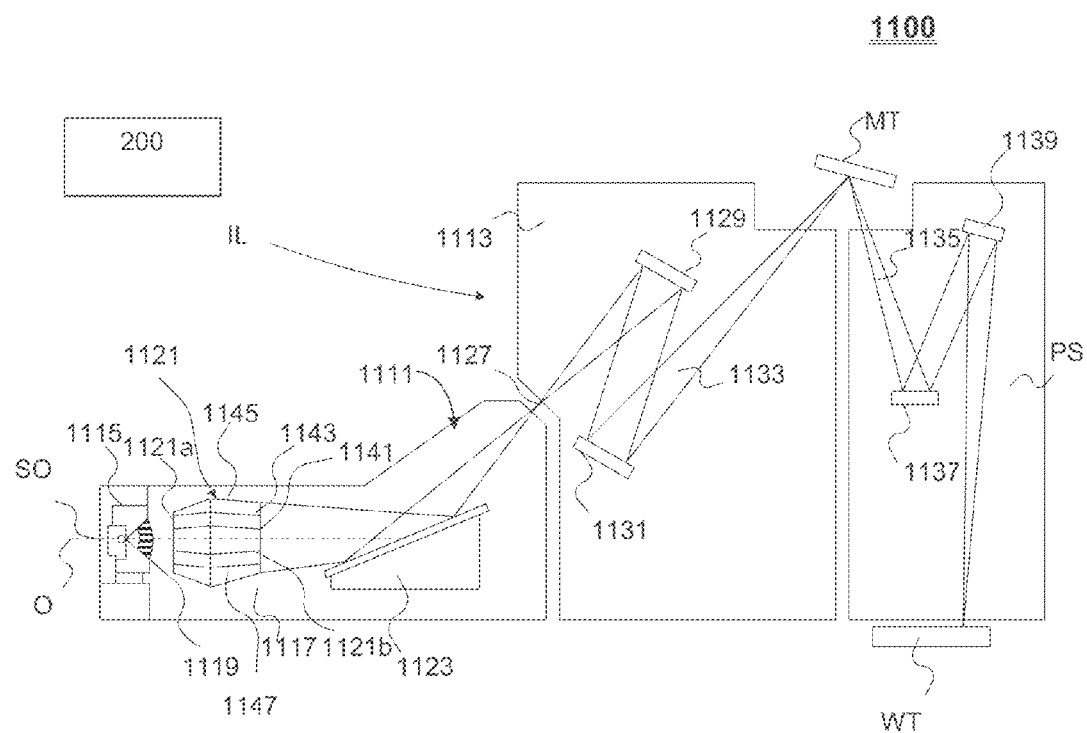

FIG. 11 depicts an example EUV lithographic apparatus.

Figure 12:
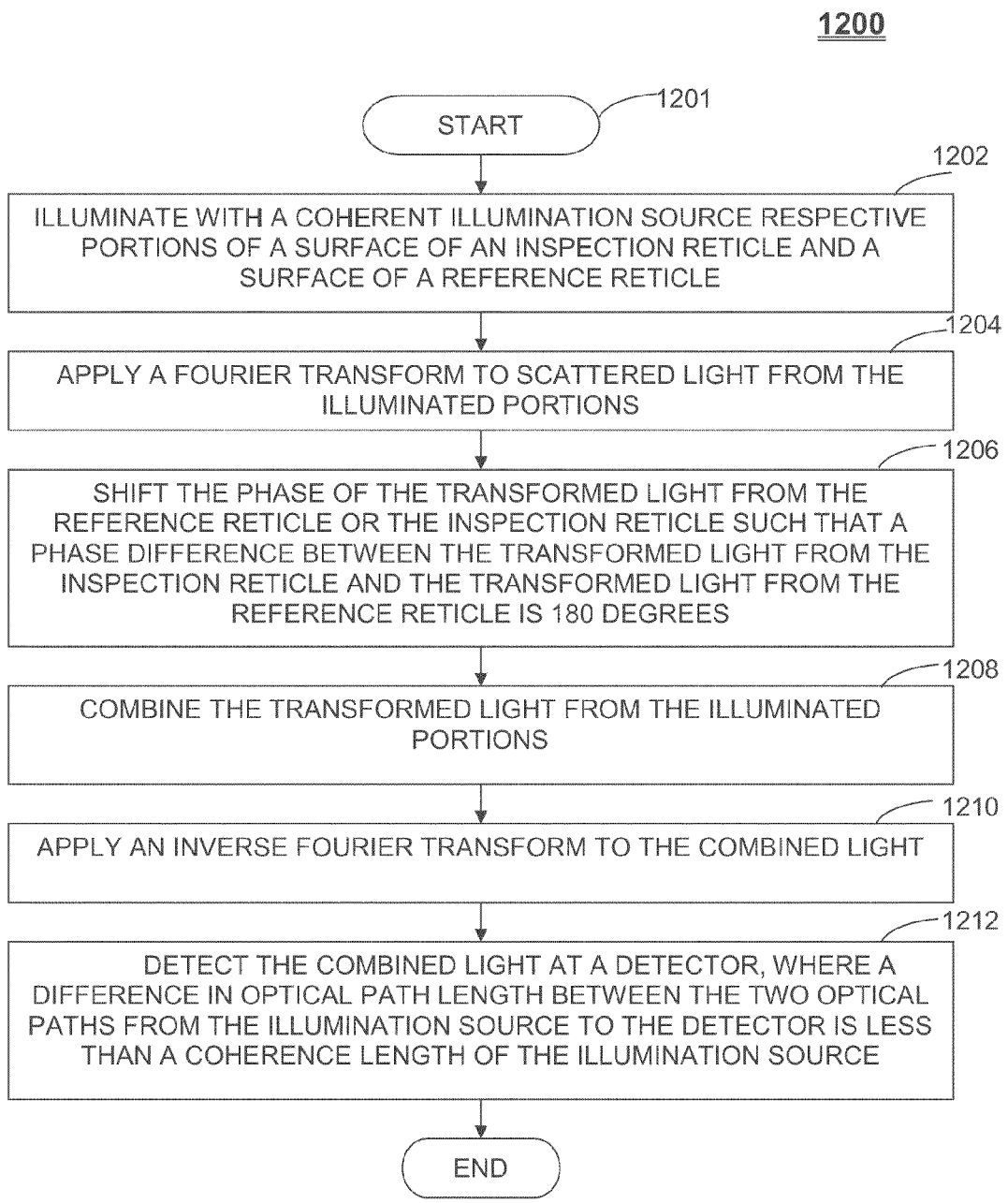

FIG. 12 is a flow diagram illustrating a method of reticle inspection, according to an embodiment of the present invention.

Figure 13:
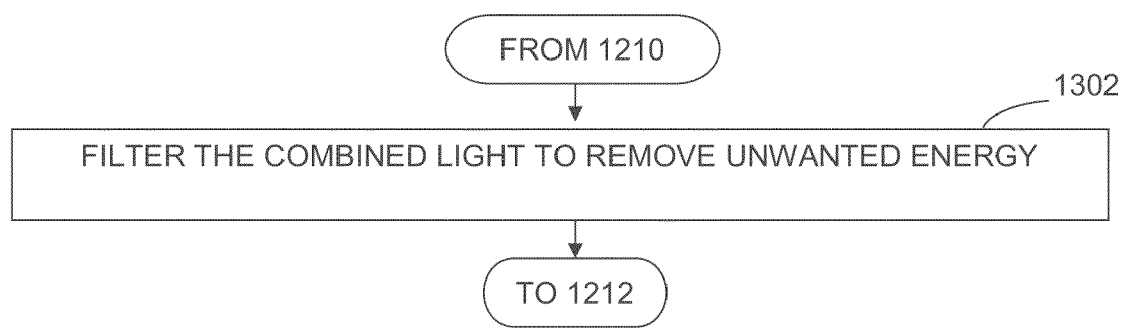

FIG. 13 is a flow diagram illustrating a further step of the reticle inspection method shown in FIG. 12, according to an embodiment of the present invention.

Figure 14:
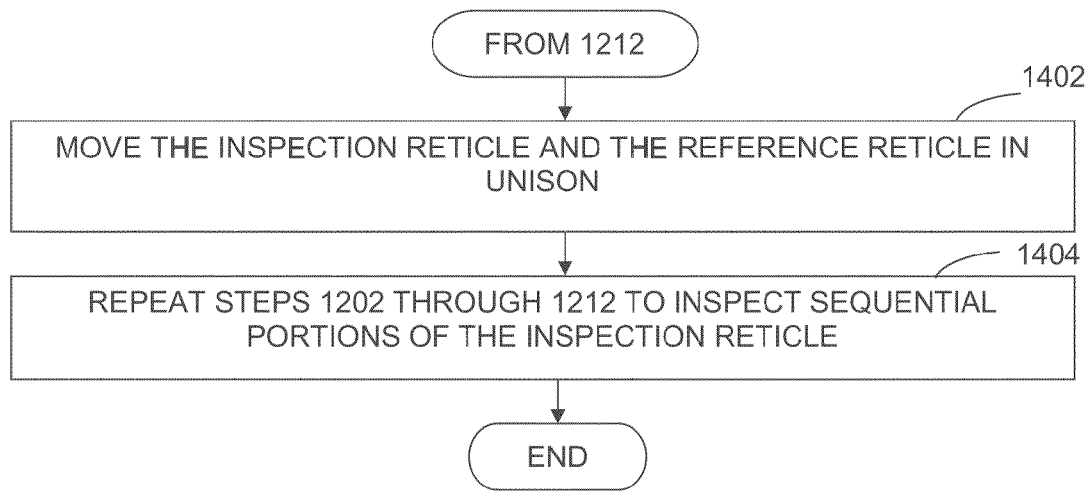

FIG. 14 is a flow diagram illustrating further steps of the reticle inspection method shown in FIG. 12, according to an embodiment of the present invention.

Figure 15:
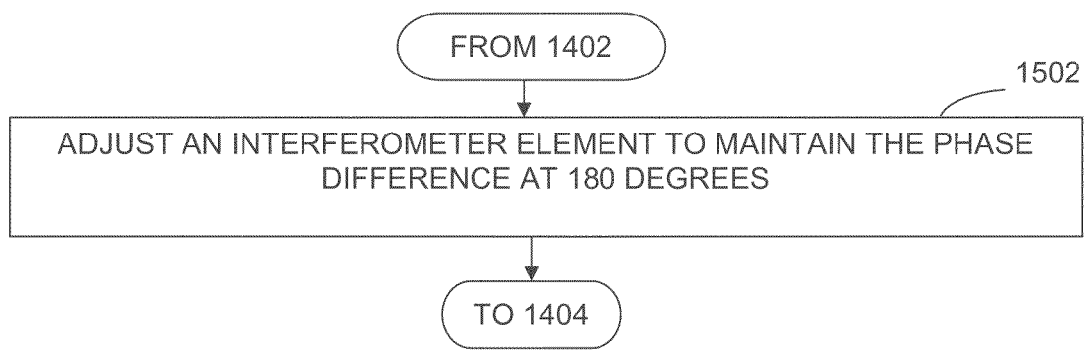

FIG. 15 is a flow diagram illustrating a further step of the reticle inspection method shown in FIG. 14, according to an embodiment of the present invention.

Figure 16:
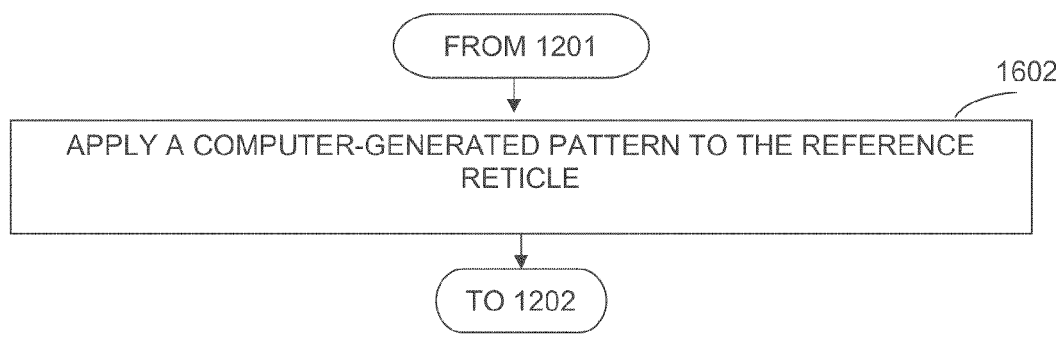

FIG. 16 is a flow diagram illustrating a further step of the reticle inspection method shown in FIG. 12, according to an embodiment of the present invention.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

I. Overview

The present invention is directed to reticle inspection systems and methods. This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

The following description presents systems and methods of reticle inspection that allow particle and defect detection on a reticle, including a reticle having an arbitrary pattern. This inspection is accomplished using highly productive means of scatterometry. The presented approach suppresses light scattered from any pattern on a reticle directly in the optical path, and as a result, is capable of detecting particles and defects using a photodetector with limited dynamic range.

II. Reticle Inspection System Embodiments

Figure 1:
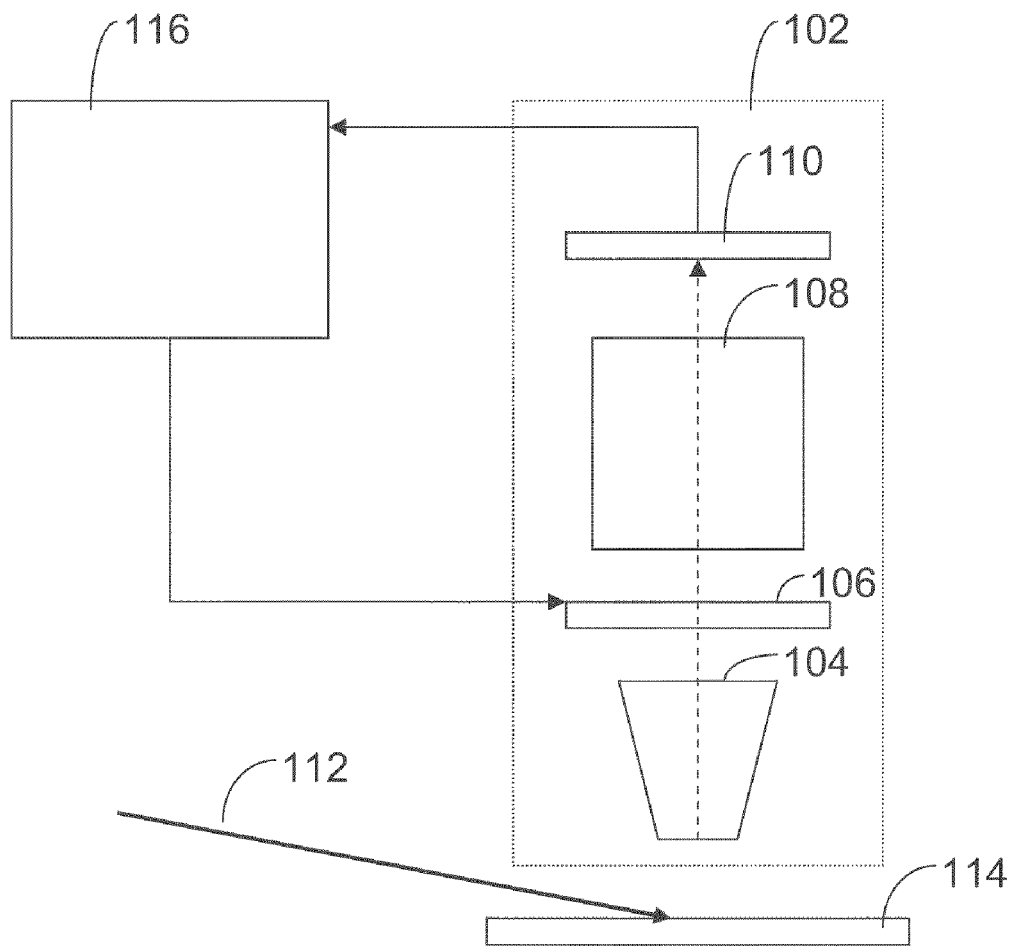
FIG. 1 is an example of a known reticle inspection system using scatterometry.
Figure 2:
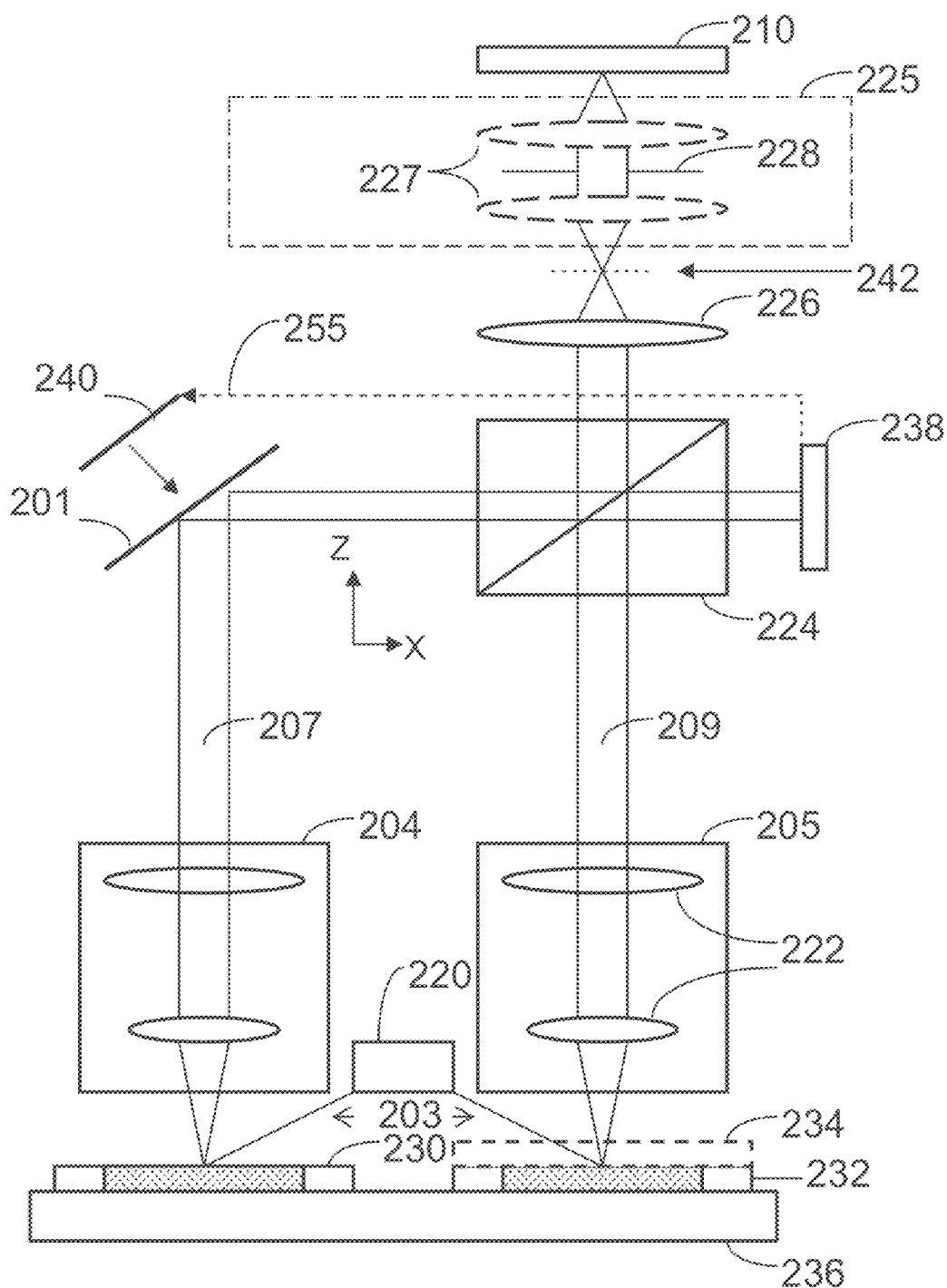
FIG. 2 depicts a reticle inspection system, according to an embodiment of the present invention.
Figure 3A:
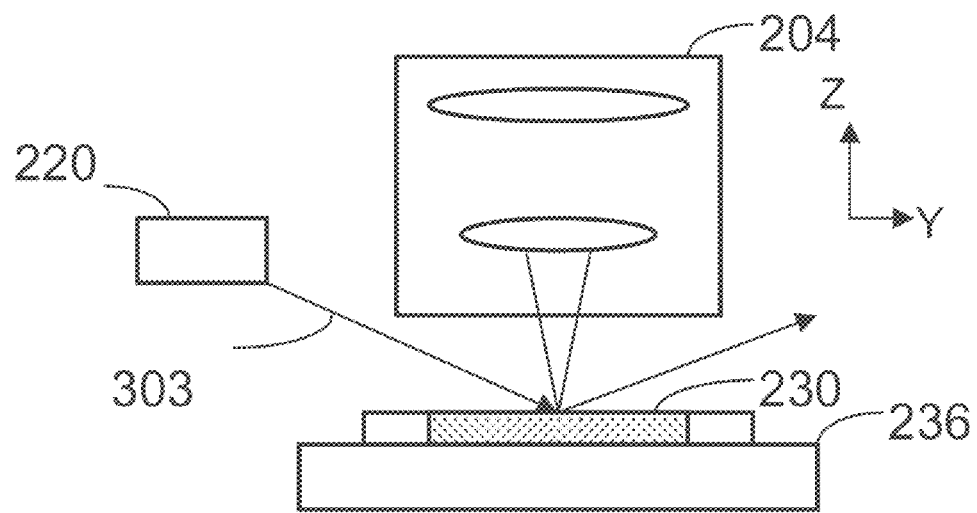
Figure 3B:
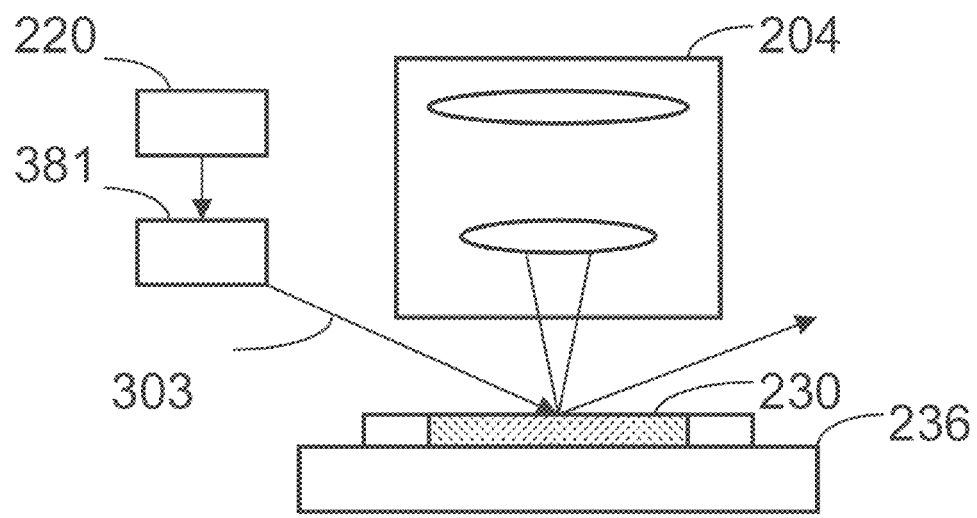
Figure 3C:
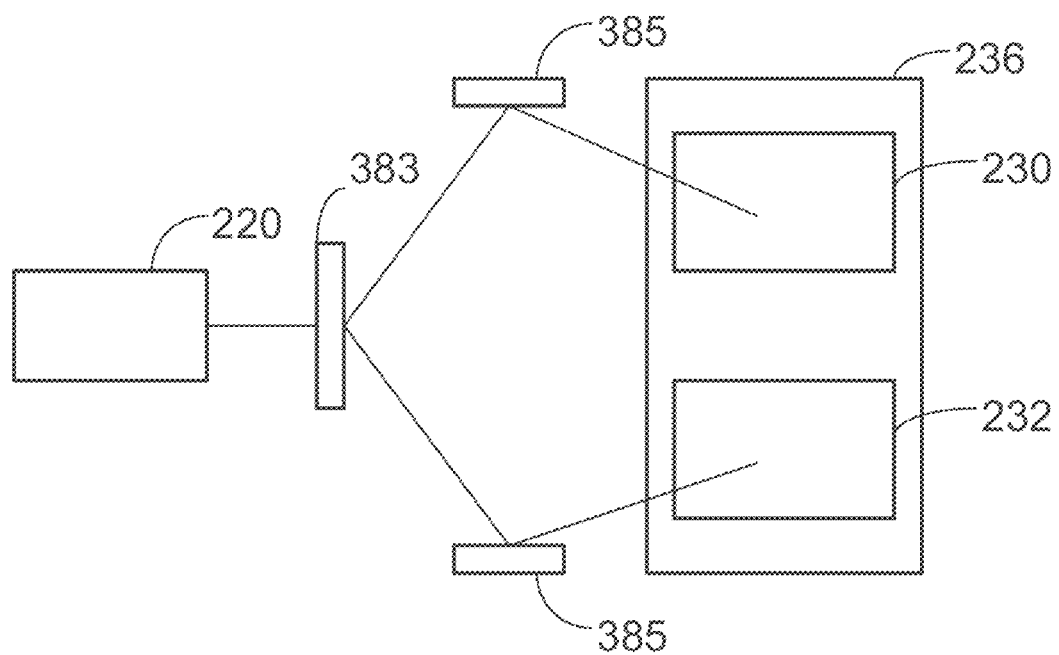
Figure 3D:
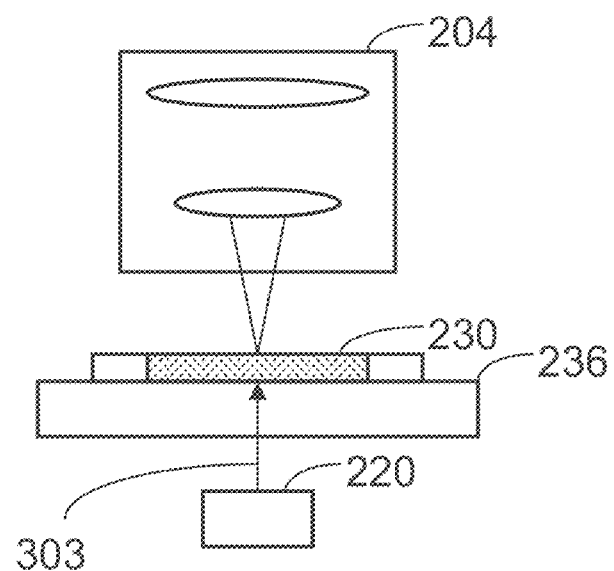

FIG. 2 schematically depicts reticle inspection system 200, according to an embodiment of the present invention. Reticle inspection system 200 includes a substrate support 236 having an inspection reticle 230 and a reference reticle 232 mounted thereon. Inspection reticle 230 is a reticle provided for inspection. Reference reticle 232 is a reticle provided for comparison to inspection reticle 230. Reference reticle 232 may include a pellicle 234 (or a glass window, for example) for protection from contamination. Inspection reticle 230 may also include a pellicle, although will not have a pellicle if used for EUV lithographic processing.

Reticle inspection system 200 also includes an illumination source 220 that provides coherent illumination beams 203 to respective equivalent portions (e.g., the same areas on identical reticles, areas having equivalent patterns, etc.) of inspection reticle 230 and reference reticle 232, and microscope objective systems 204 and 205 that respectively apply Fourier transforms to the illumination beams propagated from the illuminated inspection reticle 230 and reference reticle 232. Lens 226 later performs an inverse Fourier transform and forms images of the reticles. In an embodiment, microscope objective systems 204 and 205 can include one or more lenses. The transformed beams 207 and 209 are combined (e.g., subtracted) at a beam splitter 224. Transformed beam 207 is directed to beam splitter 224 via an interferometer element 201 (e.g., a mirror, tilt mirror, prism, etc.). Interferometer element 201, or an additional interferometer element (not shown), induces a 180-degree phase difference between beams 207 and 209. Other interferometer elements that can be used to induce this phase shift include, but are not to be limited to, one or more lenses, a beam splitter, an electro-optical light modulator, an acousto-optical light modulator, etc. Combined beams 207, 209 are directed from beam splitter 224, through Fourier lens 226 to a detector 210. Objectives 204 and 205 together with lens 226 form overlapped images of reticles 230 and 232 in optically conjugated planes at 242 and at detector 210.

In an embodiment, reticle inspection system 200 can optionally include a filtering system 225 between lens 226 and detector 210. Filtering system 225 can include, for example, two Fourier lenses 227 with a spatial filter 228 between them that cancel out unwanted radiation or energy. Using a filtering system 225 can provide a better output signal-to-noise ratio, and is especially useful when the reticle pattern has a periodic component. If a spatial filtering system 225 is not used, the photodetector 210 is positioned in plane 242.

In order to maintain the 180-degree phase difference between beams 207 and 209, an embodiment of reticle inspection system 200 can also include a feedback loop to adjust interferometer element 201. The feedback loop includes a detector 238 that detects beam 207 and provides a control signal 255 to an actuator 240. Actuator 240 can then adjust interferometer element 201 as needed for required tilt and piston. Control signal 255 can be generated from light intensity detected by detector 238. The feedback loop shown in FIG. 200 is shown in the optical path that includes the inspection reticle. However, it could also be placed in the path that includes the reference reticle.

The optical path that runs from illumination source 220 to inspection reticle 230 to detector 210 represents an inspection path or branch, and the optical path that runs from illumination source 220 to reference reticle 232 to detector 210 represents a reference path or branch. An optical path (or optical path length) is a product of geometrical length (s) and refractive index (n) as shown in the following equation: OPL=$\int n(s)ds$, where integration is along a ray. In an example case of straight rays in two branches (from the light source to the detector) with uniform mediums, the optical path difference (OPD) is equal to (n1*s1)−(n2*s2). The optical path length difference between the inspection branch and the reference branch needs to be less than the coherence length of illumination source 220. This optical path length difference can be zero, or approximately zero. For a system operating with a light source that has a short coherence length, the optical path length difference is preferably as close to zero as possible.

In the system described above, using a coherent illumination source and maintaining a 180-degree phase shift between the inspection and reference branches, the resulting image at detector 210 represents a difference in amplitude and phase distributions of the inspection reticle and the reference reticle. With this arrangement, foreign particles and/or defects are distinguishable in the image, for example, as will be described further below with reference to FIG. 9.

FIGS. 3A, 3B, 3C, 3D and 4 depict various examples of reticle illumination, according to embodiments of the present invention. In the embodiment shown in FIG. 3A, a light beam 303 is shown directly provided to inspection reticle 230 from illumination source 220. Light beam 303 can also be directly provided to reference reticle 232 in this manner, as was shown in FIG. 2. In another embodiment shown in FIG. 3B, light beam 303 is provided to inspection reticle 230 via an optional illumination system 381. In a further embodiment shown in FIG. 3C, the illumination from illumination source 220 can be split via optical element 383 (e.g., a beam splitter, a diffraction grating, etc.) and directed to reticles 230, 232 via fold mirrors 385. Although many of the embodiments described in this document are described for use with reflective reticles, the embodiments of the present invention can also be applied for use with transmissive reticles (for the inspection reticle, reference reticle, or both), as exemplified in FIG. 3D.

Figure 4:
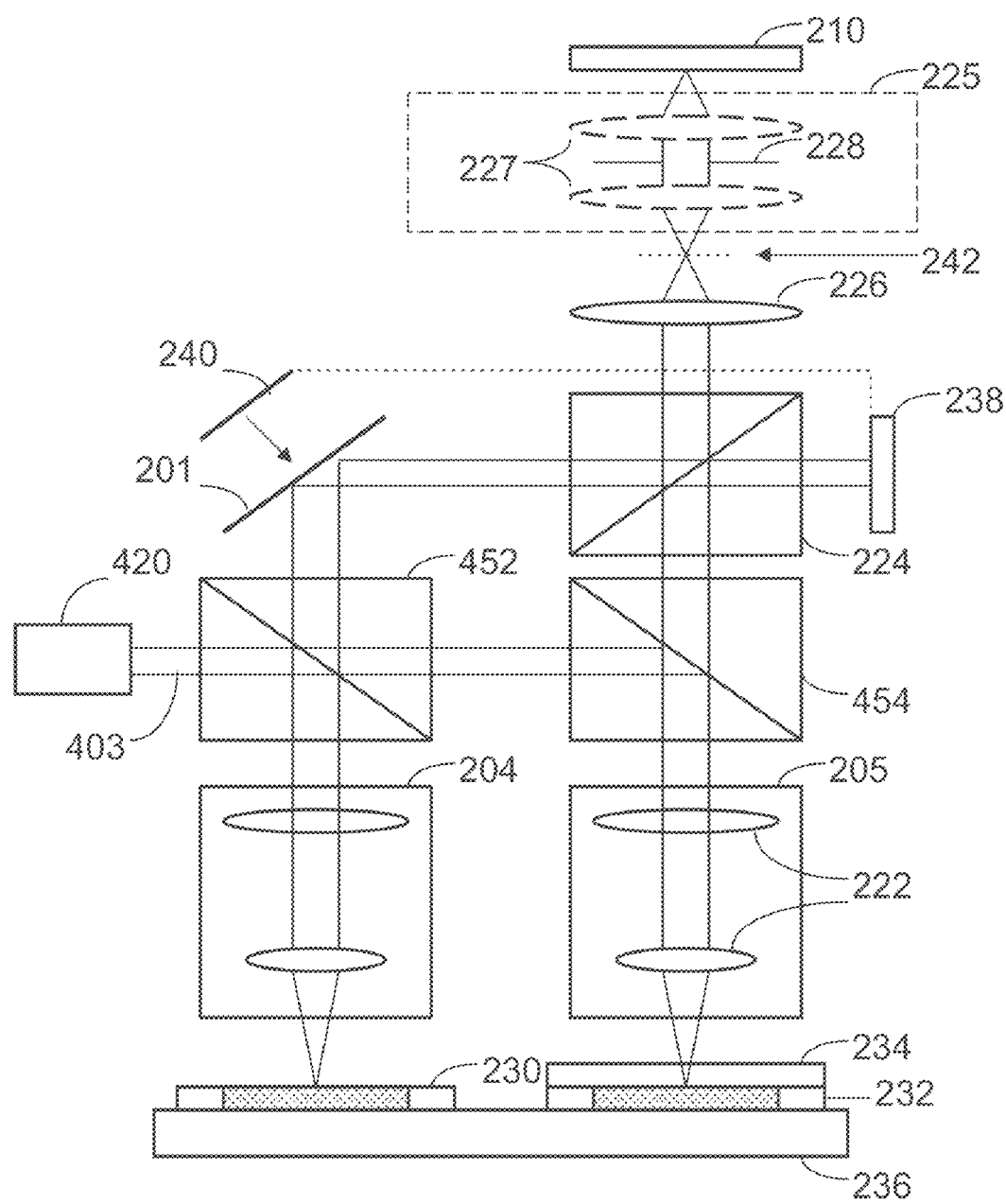

In the embodiment shown in FIG. 4, light beam 403 is provided by illumination source 420 to inspection reticle 230 and reference reticle 232 via microscope objective systems 204 and 205, respectively. In FIG. 4, this is accomplished using beam splitters 452 and 454, respectively. The embodiment shown in FIG. 4 provides high numerical aperture illumination that allows more flexibility in optimizing illumination conditions. In each of these embodiments, the coherent illumination beams form small spots in identical (or equivalent) areas of inspection reticle 230 and reference reticle 232. The spots can be on the order of $1 \times 1$ mm$^2$, $0.25 \times 0.25$ mm$^2$, etc.

In an embodiment of the present invention, reference reticle 232 can be a spatial light modulator. Examples of a spatial light modulator can include, but are not to be limited to, a liquid crystal modulator array (e.g., in visible spectral range) and a micro-mirror array (e.g., for UV systems). FIG. 5 depicts an embodiment of the present invention that includes a processor 560 that can be used to provide pattern data to reference reticle 232' for generation of a reference pattern.

FIG. 6 depicts a reticle inspection system 600 having equal optical path lengths, according to an embodiment of the present invention. Reticle inspection system 600 includes a substrate support 664 having an inspection reticle 630 and a reference reticle 632 mounted on opposite surfaces. Reticle inspection system 600 also includes an illumination source 670 that provides coherent illumination beams 603 to respective equivalent portions (e.g., the same areas on identical reticles, areas having equivalent patterns, etc.) of inspection reticle 630 and reference reticle 632. Illumination beams 603 are directed to reticles 630 and 632 via reflective elements 672 and 674, respectively (e.g., mirrors, prisms, etc.). An optical element such as a beam splitter or diffraction grating can also be used, similar to the way optical element 383 is used in FIG. 3C. Reticle inspection system 600 also includes microscope objective systems 604, 605 and lens 626 that function in a similar manner as microscope objective systems 204, 205 and lens 226 in FIG. 2. Interferometer elements 601 and 668 (e.g., mirrors, prisms, etc.), direct respective beams 607, 609 from microscope objective systems 604 and 605 to a beam splitter 624. Interferometer elements 601, 668 are configured to induce a 180-degree phase difference between beams 607 and 609. Beams 607 and 609 are combined (e.g., subtracted) at beam splitter 624. Combined beams 607, 609 are directed from beam splitter 624 through lens 626 to a detector 610.

In an embodiment, reticle inspection system 600 can optionally include a filtering system (not shown) between lens 626 and detector 610 similar to filtering system 225 in FIG. 2.

In order to maintain the 180-degree phase difference between beams 607 and 609, an embodiment of reticle inspection system 600 can also include a feedback loop to adjust interferometer element 601 similar to the feedback loop shown in FIG. 2. The feedback loop includes a detector 638 that detects beam 607 and provides a control signal 655 to an actuator 640. Actuator 640 can then adjust interferometer element 601 as needed.

In the embodiment shown in FIG. 6, the optical path length difference between the inspection and reference reticles 630, 632 and detector 610 is suitably less than a coherence length of illumination source 670. In FIG. 6, these optical path lengths are approximately, if not exactly, equal. Thus, the optical path length difference is close to, if not exactly, zero. This allows for use of a light source with a short coherence length and minimizes sensitivity to cosmetic defects on optical surfaces of the optical elements used.

As discussed above with reference to FIG. 2, the resulting image at detector 610 represents a difference in amplitude and phase distributions of the inspection reticle and the reference reticle allowing foreign particles and/or defects to be easily distinguished, as will be described further below with reference to FIG. 9.

FIGS. 7A, 7B, and 7C depict alternative examples of reticle supports, according to embodiments of the present invention. FIG. 7A shows reticle support 236 as depicted in the embodiment shown in FIG. 2. Reticle support 236 is a single support that has inspection reticle 230 mounted on one end and reference reticle 232 mounted on the other end. Reticle support 236 is a movable reticle support that allows for inspection of sequential or successive portions of inspection reticle 230. Because reticle support 236 supports both inspection reticle 230 and reference reticle 232, inspection reticle 230 and reference reticle 232 both move in unison (i.e., reticles 230 and 232 move together with identical movements as reticle support 236 is moved).

In an alternative embodiment shown in FIG. 7B, inspection reticle 230 is mounted on a first reticle support 778, and reference reticle 232 is mounted on a second reticle support 780. If two separate reticle supports 778, 780 are used, they are to be movable in unison in order to inspect sequential or successive portions of inspection reticle 230.

In another alternative embodiment shown in FIG. 7C, inspection reticle 230 is mounted on a first reticle support 782, reference reticle 232 is mounted on a second reticle support 784, and first reticle support 782 and reference reticle support 784 are both located on opposite ends of a third reticle support 786. In this embodiment, first reticle support 782 and second reticle support 784 are movable in unison to accommodate inspection of sequential or successive portions of inspection reticle 230. Third reticle support 786 is also movable to allow for more direct moves to a desired location.

While the above description discusses the reticles as movable (upon their respective supports), another embodiment of the invention includes having stationary reticles. In this embodiment, the system can move to provide inspection scanning, while the reticles remain stationary.

FIGS. 8A and 8B depict alternative examples using a single reticle, according to embodiments of the present invention. In FIG. 8A, a single reticle 831 is shown on reticle support 836. Single reticle 831 has two patterns thereon—an inspection pattern 863 and a separate reference pattern 865. In FIG. 8B, a single reticle 867 is shown on reticle support 836. Single reticle 867 has a single pattern 869 thereon. Single pattern 869 includes an inspection pattern portion 871 and a reference pattern portion 873. Inspection pattern portion 871 and reference pattern portion 873 can include identical or equivalent patterns, for example. Each embodiment in FIGS. 8A and 8B can be incorporated into reticle inspection system 200 of FIG. 2, for example, in place of inspection reticle 230, reference reticle 232, and reticle support 236.

FIG. 9 illustrates imaging examples 990, 991, and 992 (computer modeling) showing foreign particles detected using embodiments of the present invention. Examples 990 and 991 show random patterns. In example 990, inspection reticle 993 contains a particle or defect 994, and reference reticle 995 contains a particle or defect 996. Using reticle inspection system 200 (or 600) to apply mathematical subtraction, image 997 results at detector 210 (or 610) and particles 994 and 996 are both distinguishable. Because a particle or defect was found, inspection reticle 993 can be cleaned (or otherwise disposed of if unusable, for example). Since it may be unclear from image 997 whether the particles/defects were located on inspection reticle 993 or reference reticle 995, reference reticle 995 can also be cleaned or otherwise attended to. Examples 991 and 992 are similar to example 990, except that example 992 shows a regular (or periodic) pattern. In example 992, a potential particle or defect 998 does not appear in image 999 because it is identical on both the inspection and reference reticles.

As stated previously, a resulting image at detector 210 (or 610) represents a difference in amplitude and phase distributions of the inspection reticle and the reference reticle. Due to the phase shift of 180 degrees and the optical path length difference of less than a coherence length of the light source, an amplitude image from one reticle is subtracted from the amplitude image of the other, and the differences between the patterns show as bright spots in the resulting image. In mathematical simulation, this subtraction of pattern images is very efficient. However, it requires precise overlay adjustment between the two reticles and 180 degrees phase difference over the image field. The precise overlay between reticles can be provided by system initial alignment, using metrology alignment marks, and a signal minimization algorithm, for example. The required phase shift over the field of view can be provided by dynamic tilt and phase adjustment during the inspection scanning process (e.g., by controlling interferometer elements 201 and 601 in reticle inspection systems 200 and 600 as discussed above). After image subtraction, it is possible that some residual noise may be observed.

Random patterns, or patterns with a mix of regular and random components, cannot be effectively processed with the known Fourier filtering approach discussed in the Background section of this document. The present invention allows effective particle and defect detection without limitations on the pattern topology. It allows suppressing the light scattered from a pattern on the reticle directly in the optical path, and as a result, allows detection of particles and defects using a photodetector having limited dynamic range.

III. Example Lithographic Environments

The embodiments described above are depicted as separate devices.

Alternatively, they may optionally be provided as an in-tool device, that is, within a lithographic system. As a separate apparatus, it can be used for purposes of reticle inspection (e.g., prior to shipping). As an in-tool device, it can perform a quick inspection of a reticle prior to using the reticle for a lithographic process. FIGS. 10A, 10B, and 11 illustrate examples of lithographic systems that can incorporate reticle inspection system 200 as an in-tool device. In FIGS. 10A, 10B, and 11, reticle inspection system 200 is shown together with the respective lithography system.

The following description presents detailed example environments in which embodiments of the present invention may be implemented.

A. Example Reflective and Transmissive Lithographic Systems

FIGS. 10A and 10B schematically depict lithographic apparatus 1000 and lithographic apparatus 1000', respectively. Lithographic apparatus 1000 and lithographic apparatus 1000' each include: an illumination system (illuminator) IL configured to condition a radiation beam B (e.g., DUV or EUV radiation); a support structure (e.g., a mask table) MT configured to support a patterning device (e.g., a mask, a reticle, or a dynamic patterning device) MA and connected to a first positioner PM configured to accurately position the patterning device MA; and a substrate table (e.g., a wafer table) WT configured to hold a substrate (e.g., a resist coated wafer) W and connected to a second positioner PW configured to accurately position the substrate W. Lithographic apparatuses 1000 and 1000' also have a projection system PS configured to project a pattern imparted to the radiation beam B by patterning device MA onto a target portion (e.g., comprising one or more dies) C of the substrate W. In lithographic apparatus 1000 the patterning device MA and the projection system PS is reflective, and in lithographic apparatus 1000' the patterning device MA and the projection system PS is transmissive.

The illumination system IL may include various types of optical components, such as refractive, reflective, magnetic, electromagnetic, electrostatic or other types of optical components, or any combination thereof, for directing, shaping, or controlling the radiation B.

The support structure MT holds the patterning device MA in a manner that depends on the orientation of the patterning device MA, the design of the lithographic apparatuses 1000 and 1000', and other conditions, such as for example whether or not the patterning device MA is held in a vacuum environment. The support structure MT may use mechanical, vacuum, electrostatic or other clamping techniques to hold the patterning device MA. The support structure MT may be a frame or a table, for example, which may be fixed or movable, as required. The support structure MT may ensure that the patterning device is at a desired position, for example with respect to the projection system PS.

The term "patterning device" MA should be broadly interpreted as referring to any device that may be used to impart a radiation beam B with a pattern in its cross-section, such as to create a pattern in the target portion C of the substrate W. The pattern imparted to the radiation beam B may correspond to a particular functional layer in a device being created in the target portion C, such as an integrated circuit.

The patterning device MA may be transmissive (as in lithographic apparatus 1000' of FIG. 10B) or reflective (as in lithographic apparatus 1000 of FIG. 10A). Examples of patterning devices MA include reticles, masks, programmable mirror arrays, and programmable LCD panels. Masks are well known in lithography, and include mask types such as binary, alternating phase shift, and attenuated phase shift, as well as various hybrid mask types. An example of a programmable mirror array employs a matrix arrangement of small mirrors, each of which may be individually tilted so as to reflect an incoming radiation beam in different directions. The tilted mirrors impart a pattern in the radiation beam B which is reflected by the mirror matrix.

The term "projection system" PS may encompass any type of projection system, including refractive, reflective, catadioptric, magnetic, electromagnetic and electrostatic optical systems, or any combination thereof, as appropriate for the exposure radiation being used, or for other factors, such as the use of an immersion liquid or the use of a vacuum. A vacuum environment may be used for EUV or electron beam radiation since other gases may absorb too much radiation or electrons. A vacuum environment may therefore be provided to the whole beam path with the aid of a vacuum wall and vacuum pumps. A reticle inspection system such as described above can be included within the vacuum environment so that reticles can be inspected without having to remove them from the vacuum environment.

Lithographic apparatus 1000 and/or lithographic apparatus 1000' may be of a type having two (dual stage) or more substrate tables (and/or two or more mask tables) WT. In such "multiple stage" machines the additional substrate tables WT may be used in parallel, or preparatory steps may be carried out on one or more tables while one or more other substrate tables WT are being used for exposure. For example, while one mask may be used for exposure, another mask table may be used for reticle inspection using a reticle inspection system as described above.

Referring to FIGS. 10A and 10B, the illuminator IL receives a radiation beam from a radiation source SO. The source SO and the lithographic apparatuses 1000, 1000' may be separate entities, for example when the source SO is an excimer laser. In such cases, the source SO is not considered to form part of the lithographic apparatuses 1000 or 1000', and the radiation beam B passes from the source SO to the illuminator IL with the aid of a beam delivery system BD (FIG. 10B) comprising, for example, suitable directing mirrors and/or a beam expander. In other cases, the source SO may be an integral part of the lithographic apparatuses 1000, 1000'—for example when the source SO is a mercury lamp. The source SO and the illuminator IL, together with the beam delivery system BD, if required, may be referred to as a radiation system.

The illuminator IL may comprise an adjuster AD (FIG. 10B) for adjusting the angular intensity distribution of the radiation beam. Generally, at least the outer and/or inner radial extent (commonly referred to as σ-outer and σ-inner, respectively) of the intensity distribution in a pupil plane of the illuminator may be adjusted. In addition, the illuminator IL may comprise various other components (FIG. 10B), such as an integrator IN and a condenser CO. The illuminator IL may be used to condition the radiation beam B, to have a desired uniformity and intensity distribution in its cross section.

Referring to FIG. 10A, the radiation beam B is incident on the patterning device (e.g., mask) MA, which is held on the support structure (e.g., mask table) MT, and is patterned by the patterning device MA. In lithographic apparatus 1000, the radiation beam B is reflected from the patterning device (e.g., mask) MA. After being reflected from the patterning device (e.g., mask) MA, the radiation beam B passes through the projection system PS, which focuses the radiation beam B onto a target portion C of the substrate W. With the aid of the second positioner PW and position sensor IF2 (e.g., an interferometric device, linear encoder or capacitive sensor), the substrate table WT may be moved accurately, e.g. so as to position different target portions C in the path of the radiation beam B. Similarly, the first positioner PM and another position sensor IF1 may be used to accurately position the patterning device (e.g., mask) MA with respect to the path of the radiation beam B. Patterning device (e.g., mask) MA and substrate W may be aligned using mask alignment marks M1, M2 and substrate alignment marks P1, P2.

Referring to FIG. 10B, the radiation beam B is incident on the patterning device (e.g., mask MA), which is held on the support structure (e.g., mask table MT), and is patterned by the patterning device. Having traversed the mask MA, the radiation beam B passes through the projection system PS, which focuses the beam onto a target portion C of the substrate W. With the aid of the second positioner PW and position sensor IF (e.g., an interferometric device, linear encoder or capacitive sensor), the substrate table WT can be moved accurately, e.g. so as to position different target portions C in the path of the radiation beam B. Similarly, the first positioner PM and another position sensor (which is not explicitly depicted in FIG. 10B) can be used to accurately position the mask MA with respect to the path of the radiation beam B, e.g., after mechanical retrieval from a mask library, or during a scan.

In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (known as scribe-lane alignment marks). Similarly, in situations in which more than one die is provided on the mask MA, the mask alignment marks may be located between the dies.

The lithographic apparatuses 1000 and 1000' may be used in at least one of the following modes:

1. In step mode, the support structure (e.g., mask table) MT and the substrate table WT are kept essentially stationary, while an entire pattern imparted to the radiation beam B is projected onto a target portion C at one time (i.e., a single static exposure). The substrate table WT is then shifted in the X and/or Y direction so that a different target portion C may be exposed.

2. In scan mode, the support structure (e.g., mask table) MT and the substrate table WT are scanned synchronously while a pattern imparted to the radiation beam B is projected onto a target portion C (i.e., a single dynamic exposure). The velocity and direction of the substrate table WT relative to the support structure (e.g., mask table) MT may be determined by the (de-)magnification and image reversal characteristics of the projection system PS.

3. In another mode, the support structure (e.g., mask table) MT is kept substantially stationary holding a programmable patterning device, and the substrate table WT is moved or scanned while a pattern imparted to the radiation beam B is projected onto a target portion C. A pulsed radiation source SO may be employed and the programmable patterning device is updated as required after each movement of the substrate table WT or in between successive radiation pulses during a scan. This mode of operation may be readily applied to maskless lithography that utilizes programmable patterning device, such as a programmable mirror array of a type as referred to herein.

Combinations and/or variations on the described modes of use or entirely different modes of use may also be employed.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin-film magnetic heads, etc. The skilled artisan will appreciate that, in the context of such alternative applications, any use of the terms "wafer" or "die" herein may be considered as synonymous with the more general terms "substrate" or "target portion," respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

In a further embodiment, lithographic apparatus 1000 includes an extreme ultraviolet (EUV) source, which is configured to generate a beam of EUV radiation for EUV lithography. In general, the EUV source is configured in a radiation system (see below), and a corresponding illumination system is configured to condition the EUV radiation beam of the EUV source.

B. Example EUV Lithographic Apparatus

FIG. 11 schematically depicts an exemplary EUV lithographic apparatus 1100 according to an embodiment of the present invention. As discussed previously, reticle inspection is especially important for EUV reticles that are not protected by pellicles. Integrating a reticle inspection system as presented herein with an EUV lithographic apparatus would be beneficial.

In FIG. 11, EUV lithographic apparatus 1100 includes a radiation system 1111, an illumination optics unit 1113, and a projection system PS. The radiation system 1111 includes a radiation source SO, in which a beam of radiation may be formed by a discharge plasma. In an embodiment, EUV radiation may be produced by a gas or vapor, for example, from Xe gas, Li vapor, or Sn vapor, in which a very hot plasma is created to emit radiation in the EUV range of the electromagnetic spectrum. The very hot plasma can be created by generating at least partially ionized plasma by, for example, an electrical discharge. Partial pressures of, for example, 10 Pa of Xe, Li, Sn vapor or any other suitable gas or vapor may be required for efficient generation of the radiation. The radiation emitted by radiation source SO is passed from a source chamber 1115 into a collector chamber 1117 via a gas barrier or contaminant trap 1119 positioned in or behind an opening in source chamber 1115. In an embodiment, gas barrier 1119 may include a channel structure.

Collector chamber 1117 includes a radiation collector 1121 (which may also be called collector mirror or collector) that may be formed from a grazing incidence collector. Radiation collector 1121 has an upstream radiation collector side 1121*a* and a downstream radiation collector side 1121*b*, and radiation passed by collector 1121 can be reflected off a grating spectral filter 1123 to be focused at a virtual source point 1127 at an aperture in the collector chamber 1117. Radiation collectors 1121 are known to skilled artisans.

From collector chamber 1117, a beam of radiation 1133 is reflected in illumination optics unit 1113 via normal incidence reflectors 1129 and 1131 onto a reticle or mask (not shown) positioned on reticle or mask table MT. A patterned beam 1135 is formed, which is imaged in projection system PS via reflective elements 1137 and 1139 onto a substrate (not shown) supported on wafer stage or substrate table WT. In various embodiments, illumination optics unit 1113 and projection system PS may include more (or fewer) elements than depicted in FIG. 11. For example, grating spectral filter 1123 may optionally be present, depending upon the type of lithographic apparatus. Further, in an embodiment, illumination optics unit 1113 and projection system PS may include more mirrors than those depicted in FIG. 11. For example, projection system PS may incorporate one to four reflective elements in addition to reflective elements 1137 and 1139. In FIG. 11, reference number 1147 indicates a space between two reflectors, e.g., a space between reflectors 1141 and 1143.

In an embodiment, collector mirror 1121 may also include a normal incidence collector in place of or in addition to a grazing incidence mirror. Further, collector mirror 1121, although described in reference to a nested collector with reflectors 1141, 1143, and 1145, is herein further used as example of a collector.

Further, instead of a grating 1123, as schematically depicted in FIG. 11, a transmissive optical filter may also be applied. Optical filters transmissive for EUV, as well as optical filters less transmissive for or even substantially absorbing UV radiation, are known to skilled artisans. Hence, the use of "grating spectral purity filter" is herein further indicated interchangeably as a "spectral purity filter," which includes gratings or transmissive filters. Although not depicted in FIG. 11, EUV transmissive optical filters may be included as additional optical elements, for example, configured upstream of collector mirror 1121 or optical EUV transmissive filters in illumination unit 1113 and/or projection system PS.

The terms "upstream" and "downstream," with respect to optical elements, indicate positions of one or more optical elements "optically upstream" and "optically downstream," respectively, of one or more additional optical elements. Following the light path that a beam of radiation traverses through lithographic apparatus 1100, a first optical element closer to source SO than a second optical element is configured upstream of the second optical element; the second optical element is configured downstream of the first optical element. For example, collector mirror 1121 is configured upstream of spectral filter 1123, whereas optical element 1129 is configured downstream of spectral filter 1123.

All optical elements depicted in FIG. 11 (and additional optical elements not shown in the schematic drawing of this embodiment) may be vulnerable to deposition of contaminants produced by source SO, for example, Sn. Such may be the case for the radiation collector 1121 and, if present, the spectral purity filter 1123. Hence, a cleaning device may be employed to clean one or more of these optical elements, as well as a cleaning method may be applied to those optical elements, but also to normal incidence reflectors 1129 and 1131 and reflective elements 1137 and 1139 or other optical elements, for example additional mirrors, gratings, etc.

Radiation collector 1121 can be a grazing incidence collector, and in such an embodiment, collector 1121 is aligned along an optical axis O. The source SO, or an image thereof, may also be located along optical axis O. The radiation collector 1121 may comprise reflectors 1141, 1143, and 1145 (also known as a "shell" or a Wolter-type reflector including several Wolter-type reflectors). Reflectors 1141, 1143, and 1145 may be nested and rotationally symmetric about optical axis O. In FIG. 11, an inner reflector is indicated by reference number 1141, an intermediate reflector is indicated by reference number 1143, and an outer reflector is indicated by reference number 1145. The radiation collector 1121 encloses a certain volume, i.e., a volume within the outer reflector(s) 1145. Usually, the volume within outer reflector(s) 1145 is circumferentially closed, although small openings may be present.

Reflectors 1141, 1143, and 1145 respectively may include surfaces of which at least portion represents a reflective layer or a number of reflective layers. Hence, reflectors 1141, 1143, and 1145 (or additional reflectors in the embodiments of radiation collectors having more than three reflectors or shells) are at least partly designed for reflecting and collecting EUV radiation from source SO, and at least part of reflectors 1141, 1143, and 1145 may not be designed to reflect and collect EUV radiation. For example, at least part of the back side of the reflectors may not be designed to reflect and collect EUV radiation. On the surface of these reflective layers, there may in addition be a cap layer for protection or as optical filter provided on at least part of the surface of the reflective layers.

The radiation collector 1121 may be placed in the vicinity of the source SO or an image of the source SO. Each reflector 1141, 1143, and 1145 may comprise at least two adjacent reflecting surfaces, the reflecting surfaces further from the source SO being placed at smaller angles to the optical axis O than the reflecting surface that is closer to the source SO. In this way, a grazing incidence collector 1121 is configured to generate a beam of (E)UV radiation propagating along the optical axis O. At least two reflectors may be placed substantially coaxially and extend substantially rotationally symmetric about the optical axis O. It should be appreciated that radiation collector 1121 may have further features on the external surface of outer reflector 1145 or further features around outer reflector 1145, for example a protective holder, a heater, etc.

In the embodiments described herein, the terms "lens" and "lens element," where the context allows, may refer to any one or combination of various types of optical components, comprising refractive, reflective, magnetic, electromagnetic and electrostatic optical components.

Further, the terms "radiation" and "beam" used herein encompass all types of electromagnetic radiation, comprising ultraviolet (UV) radiation (e.g., having a wavelength λ of 365, 248, 193, 157 or 126 nm), extreme ultra-violet (EUV or soft X-ray) radiation (e.g., having a wavelength in the range of 5-20 nm, e.g., 13.5 nm), or hard X-ray working at less than 5 nm, as well as particle beams, such as ion beams or electron beams. Generally, radiation having wavelengths between about 780-3000 nm (or larger) is considered IR radiation. UV refers to radiation with wavelengths of approximately 100-400 nm. Within lithography, it is usually also applied to the wavelengths, which can be produced by a mercury discharge lamp: G-line 436 nm; H-line 405 nm; and/or I-line 365 nm. Vacuum UV, or VUV (i.e., UV absorbed by air), refers to radiation having a wavelength of approximately 100-200 nm. Deep UV (DUV) generally refers to radiation having wavelengths ranging from 126 nm to 428 nm, and in an embodiment, an excimer laser can generate DUV radiation used within lithographic apparatus. It should be appreciated that radiation having a wavelength in the range of, for example, 5-20 nm relates to radiation with a certain wavelength band, of which at least part is in the range of 5-20 nm.

IV. Reticle Inspection Method

FIG. 12 is a flow diagram illustrating a method 1200 of reticle inspection, according to an embodiment of the present invention. Method 1200 starts at step 1201 and immediately proceeds to step 1202 where respective portions of a surface of an inspection reticle and a surface of a reference reticle are illuminated by a coherent illumination source. In step 1204, a Fourier transform is applied to scattered light from the inspection reticle and to scattered light from the reference reticle. In step 1206, the phase of the transformed light from either the inspection reticle or the reference reticle is shifted such that the phase difference between the transformed light from the inspection reticle and the transformed light from the reference reticle is 180 degrees. In step 1208, the transformed light is combined such that the images that each carries subtract. In step 1210, an inverse Fourier transform is applied to the combined light. In step 1212, the combined light is detected at a detector, where the difference in optical path length between the two optical paths from the illumination source to the detector (one path via the inspection reticle and one path via the reference reticle) is less than a coherence length of the illumination source. Method 1200 then ends. In method 1200, the use of a coherent illumination source and a 180-degree phase shift between the inspection and reference branches results in an image at the detector that represents a difference in amplitude and phase distributions of the inspection reticle and the reference reticle. This arrangement allows foreign particles and/or defects to be easily distinguished.

FIG. 13 is a flow diagram illustrating a further step of the reticle inspection method 1200 shown in FIG. 12, according to an embodiment of the present invention. Step 1302 stems from step 1210. In step 1302, the combined light is filtered to remove unwanted energy. For example, a Fourier filtering system can be used. Such filtering can provide a better output signal-to-noise ratio. The method then continues to step 1212.

FIG. 14 is a flow diagram illustrating further steps of the reticle inspection method 1200 shown in FIG. 12, according to an embodiment of the present invention. Step 1402 stems from step 1210. In step 1402, the inspection reticle and the reference reticle are moved in unison (i.e., they move together with identical movements). In step 1404, steps 1202 through 1212 are repeated to inspect sequential portions of the inspection reticle. The method then ends. This represents the scanning of the inspection reticle in sequential steps.

FIG. 15 is a flow diagram illustrating a further step of the reticle inspection method shown in FIG. 14, according to an embodiment of the present invention. Step 1502 stems from step 1402. In step 1502, an interferometer element is adjusted to maintain the phase difference at 180 degrees. The method then continues at step 1404.

FIG. 16 is a flow diagram illustrating a further step of the reticle inspection method 1200 shown in FIG. 12, according to an embodiment of the present invention. Step 1602 stems from step 1201. In step 1602, a computer-generated pattern is applied to the reference reticle. In this embodiment, the reference reticle is a spatial light modulator, such as a micro-mirror array. The method then continues at step 1202.

V. Conclusion

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A reticle inspection system, comprising:
a coherent illumination source configured to illuminate respective portions of an inspection reticle and a reference reticle;
an inspection interferometer branch having a first microscope objective system configured to apply a first Fourier transform to a first light beam propagated from the illuminated portion of the inspection reticle;
a reference interferometer branch having a second microscope objective system configured to apply a second Fourier transform to a second light beam propagated from the illuminated portion of the reference reticle;
a beam splitter configured to receive and combine the first and second light beams;
an interferometer element in the inspection interferometer branch, the interferometer element configured to induce a 180-degree phase shift between the inspection interferometer branch and the reference interferometer branch and to direct the first light beam from the first microscope objective system to the beam splitter;
a Fourier lens configured to provide an inverse Fourier transform to the combined first and second light beams whereby an image is formed; and
a detector configured to detect the image, the image representing a difference in amplitude and phase distributions of the inspection reticle and the reference reticle,
wherein the inspection interferometer branch has an optical path between the illumination source and the detector and the reference interferometer branch has an optical path between the illumination source and the detector, and
wherein an optical path length difference between the inspection interferometer branch and the reference interferometer branch is less than a coherence length of the illumination source.

2. The reticle inspection system of claim 1, further comprising:
a filtering system configured to block unwanted energy in the combined first and second light beams propagated from the Fourier lens.

3. The reticle inspection system of claim 1, further comprising:
a phase adjustment detector configured to detect the first light beam directed from the interferometer element and output a phase adjustment signal; and
an actuator configured to receive the phase adjustment signal from the phase adjustment detector and adjust the interferometer element in response to the phase adjustment signal.

4. The reticle inspection system of claim 1, further comprising:
an interferometer element in the reference interferometer branch, the interferometer element in the reference interferometer branch configured to direct the second light beam from the second microscope objective system to the beam splitter.

5. The reticle inspection system of claim 1, wherein the reference reticle is a spatial light modulator (SLM).

6. The reticle inspection system of claim 5, wherein the reference reticle is a micro-mirror array.

7. The reticle inspection system of claim 5, further comprising:
a processor configured to provide pattern data to the reference reticle for generation of a reference pattern.

8. The reticle inspection system of claim 1, further comprising:
a movable platform having the inspection reticle and the reference reticle mounted thereon, the movable platform configured to be moved for inspection of sequential portions of the inspection reticle.

9. The reticle inspection system of claim 8, wherein:
the inspection reticle is mounted on a first end of a surface of the movable platform, and
the reference reticle is mounted on a second end of the surface of the movable platform.

10. The reticle inspection system of claim 8, wherein:
the inspection reticle is mounted on a first surface of the movable platform, and
the reference reticle is mounted on a second surface of the movable platform, the second surface opposite to the first surface.

11. The reticle inspection system of claim 1, further comprising:
a first movable platform having the inspection reticle mounted thereon; and
a second movable platform having the reference reticle mounted thereon, the second movable platform configured to move in unison with the first movable platform, such that movements of the first movable platform and second movable platform are identical for inspection of sequential portions of the inspection reticle.

12. The reticle inspection system of claim 1, further comprising:
a first movable platform having the inspection reticle mounted thereon;
a second movable platform having the reference reticle mounted thereon, the second movable platform configured to move in unison with the first movable platform, such that movements of the first movable platform and second movable platform are identical for inspection of sequential portions of the inspection reticle; and
a third movable platform having the first movable platform and the second movable platform located thereon, the third movable platform configured to move the first and second movable platforms to a desired location.

13. The reticle inspection system of claim 1, further comprising:
a first illumination beam splitter configured to direct illumination from the illumination source to the inspection reticle through the first microscope objective system; and
a second illumination beam splitter configured to direct illumination from the illumination source to the reference reticle through the second microscope objective system.

14. A reticle inspection system, comprising:
a coherent illumination source configured to illuminate respective portions of an inspection reticle and a reference reticle;
a first reflective element configured to direct illumination from the illumination source to the inspection reticle;
a second reflective element configured to direct illumination from the illumination source to the reference reticle;
an inspection interferometer branch having a first microscope objective system configured to apply a first Fourier transform to a first light beam propagated from the illuminated portion of the inspection reticle;
a reference interferometer branch having a second microscope objective system configured to apply a second Fourier transform to a second light beam propagated from the illuminated portion of the reference reticle;

a beam splitter configured to receive and combine the first and second light beams;

a first interferometer element configured to induce a 180-degree phase shift between the inspection interferometer branch and the reference interferometer branch and to direct the first light beam from the first microscope objective system to the beam splitter;

a second interferometer element configured to direct the second light beam from the second microscope objective system to the beam splitter;

a Fourier lens configured to provide an inverse Fourier transform to the combined first and second light beams whereby an image is formed; and a detector configured to detect the image, the image representing a difference in amplitude and phase distributions of the inspection reticle and the reference reticle, wherein the inspection interferometer branch has an optical path between the illumination source and the detector and the reference interferometer branch has an optical path between the illumination source and the detector, and wherein an optical path length difference between the inspection interferometer branch and the reference interferometer branch is less than a coherence length of the illumination source.

15. A lithography system having a reticle inspection system, the reticle inspection system comprising:

a coherent illumination source configured to illuminate respective portions of an inspection reticle and a reference reticle;

an inspection interferometer branch having a first microscope objective system configured to apply a first Fourier transform to a first light beam propagated from the illuminated portion of the inspection reticle;

a reference interferometer branch having a second microscope objective system configured to apply a second Fourier transform to a second light beam propagated from the illuminated portion of the reference reticle;

a beam splitter configured to receive and combine the first and second light beams;

an interferometer element in the inspection interferometer branch, the interferometer element configured to induce a 180-degree phase shift between the inspection interferometer branch and the reference interferometer branch and to direct the first light beam from the first microscope objective system to the beam splitter;

a Fourier lens configured to provide an inverse Fourier transform to the combined first and second light beams whereby an image is formed; and a detector configured to detect the image, the image representing a difference in amplitude and phase distributions of the inspection reticle and the reference reticle, wherein the inspection interferometer branch has an optical path between the illumination source and the detector and the reference interferometer branch has an optical path between the illumination source and the detector, and wherein an optical path length difference between the inspection interferometer branch and the reference interferometer branch is less than a coherence length of the illumination source.

16. A method of inspecting a reticle, comprising:

illuminating with a coherent illumination source respective portions of a surface of an inspection reticle and a surface of a reference reticle;

applying a Fourier transform to scattered light from the illuminated portions;

shifting the phase of the transformed light from one of the inspection reticle and the reference reticle such that a phase difference between the transformed light from the inspection reticle and the transformed light from the reference reticle is 180 degrees;

combining the transformed light from the illuminated portions;

applying an inverse Fourier transform to the combined light; and detecting the combined light at a detector, wherein an optical path length difference between a first optical path between the illumination source and the detector via the inspection reticle and a second optical path between the illumination source and the detector via the reference reticle is less than a coherence length of the illumination source; and wherein the combined light detected by the detector is in the form of an image representing a difference in amplitude distributions of the inspection reticle and the reference reticle.

17. The method of claim 16, further comprising:

filtering the combined light to remove unwanted energy.

18. The method of claim 16, further comprising:

moving the inspection reticle and the reference reticle in unison in sequential steps; and repeating the illuminating, applying Fourier transform, shifting, combining, applying an inverse Fourier transform, and detecting steps to inspect sequential portions of the inspection reticle.

19. The method of claim 18, further comprising:

adjusting an interferometer element to maintain the phase difference at 180 degrees.

20. The method of claim 16, further comprising:

applying a computer-generated pattern to the reference reticle.

* * * * *